US010835635B2

United States Patent
Hanes et al.

(10) Patent No.: US 10,835,635 B2
(45) Date of Patent: Nov. 17, 2020

(54) NATURAL POLYMER BASED TISSUE ADHESIVE WITH HEALING PROMOTING PROPERTIES

(71) Applicant: HCS Innovation, LLC, Union Grove, AL (US)

(72) Inventors: Ronnie Michael Hanes, Union Grove, AL (US); Adele Lamping Hanes, Union Grove, AL (US)

(73) Assignee: HCS Innovation, LLC, Union Grove, AL (US)

( * ) Notice: Subject to any disclaimer, the term of this patent is extended or adjusted under 35 U.S.C. 154(b) by 0 days.

(21) Appl. No.: 15/994,140

(22) Filed: May 31, 2018

(65) Prior Publication Data

US 2019/0038798 A1 Feb. 7, 2019

Related U.S. Application Data

(60) Provisional application No. 62/605,185, filed on Aug. 4, 2017.

(51) Int. Cl.
| | |
|---|---|
| *A61L 24/04* | (2006.01) |
| *C09J 105/04* | (2006.01) |
| *C09J 105/08* | (2006.01) |
| *C08L 5/04* | (2006.01) |
| *C08L 5/08* | (2006.01) |
| *A61L 24/08* | (2006.01) |
| *A61L 24/00* | (2006.01) |
| *C09J 105/00* | (2006.01) |

(52) U.S. Cl.
CPC .......... *A61L 24/043* (2013.01); *A61L 24/001* (2013.01); *A61L 24/0026* (2013.01); *A61L 24/08* (2013.01); *C09J 105/00* (2013.01); *C09J 105/04* (2013.01); *C09J 105/08* (2013.01); *A61L 2400/04* (2013.01); *C08L 5/04* (2013.01); *C08L 5/08* (2013.01)

(58) Field of Classification Search
None
See application file for complete search history.

(56) References Cited

U.S. PATENT DOCUMENTS

| | | | |
|---|---|---|---|
| 5,428,014 | A | 6/1995 | Labroo et al. |
| 6,341,608 | B1 | 1/2002 | Akervall |
| 8,795,713 | B2 | 8/2014 | Makower et al. |
| 8,829,075 | B2 | 9/2014 | Bianco-Peled et al. |
| 9,381,270 | B2 | 7/2016 | Makower et al. |
| 2007/0167971 | A1 | 7/2007 | Huey et al. |
| 2008/0215090 | A1 | 9/2008 | Gonzales et al. |
| 2009/0291912 | A1 | 11/2009 | Tijsma et al. |
| 2010/0152730 | A1 | 6/2010 | Makower et al. |
| 2011/0015759 | A1* | 1/2011 | Bianco-Peled ....... A61L 15/585 623/23.72 |
| 2012/0108509 | A1 | 5/2012 | Hissong et al. |
| 2013/0018320 | A1 | 1/2013 | McKay |
| 2014/0296293 | A1 | 10/2014 | Andersen et al. |
| 2016/0008513 | A1 | 1/2016 | Cherry et al. |
| 2016/0151532 | A1 | 6/2016 | Rubin et al. |
| 2017/0326171 | A1 | 11/2017 | Diehn et al. |

FOREIGN PATENT DOCUMENTS

| | | |
|---|---|---|
| WO | WO 2013/078550 | 6/2013 |
| WO | WO 2014/172703 | 10/2014 |

OTHER PUBLICATIONS

Wang et al. Feasibility of chitosan-alginate (Chi-Alg) hydrogel used as scaffold for neural tissue engineering: a pilot study (Year: 2017).*
Feldman, "Adhesion and Hemostasis in Surgery", Encyclopedia of Materials: Science and Technology, 2001, pp. 38-43, (Year: 2001).*
El-Kamel, Amal et al., Chitosan and Sodium Alginate-Based Bioadhesive Vaginal Tablets, AAPS PharmSci, vol. 4, No. 4, Article 44, 2002, pp. 1-7.
Honary, Soheila et al., The effect of chitosan molecular weight on the properties of alginate/chitosan microparticles containing prednisolone, Tropical Journal of Pharmaceutical Research, vol. 8, No. 1, 2009, pp. 53-61.
Kucharska, Magdalena et al., Dressing Sponges Made of Chitosan and Chitosan-Alginate Fibrids, Fibres & Textiles in Eastern Europe, vol. 16, No. 3, 2008, pp. 109-113.
Murakami, Kaoru et al., Hydrogel blends of chitin/chitosan, fucoidan and alginate as healing-impaired wound dressings, Biomaterials, vol. 31, No. 1, 2010, pp. 83-90.
Vakalopoulos, Konstantinos Aristotelis et al., Mechanical Strength and Rheological Properties of Tissue Adhesives With Regard to Colorectal Anastomosis: An Ex Vivo Study, Annals of Surgery, vol. 261, No. 2, 2015, pp. 323-331.
Wu, Yu et al., A soft tissue adhesive based on aldehyde-sodium alginate and amino-carboxymethyl chitosan preparation through the Schiff reaction, Frontiers of Material Science, vol. 11, No. 3, 2017, pp. 215-222.

(Continued)

*Primary Examiner* — Kyung S Chang
(74) *Attorney, Agent, or Firm* — Pandiscio & Pandisciso

(57) ABSTRACT

A tissue adhesive with healing promotion properties formed from a mixture of natural polymers and an activating agent that enhances the adhesive properties of the natural polymer mixture is described. Use of an activating agent and a combination of the natural polymers is unique. The natural polymer tissue adhesive may be useful as a post-operative application for tonsillectomy or adenoidectomy surgery, as an internal tissue adhesive for surgery or wound repair or for application to a burn or skin donor site. For internal use, an optional treatment to improve resistance of the activated adhesive to body fluids is also described. The adhesive described not only functions as an adhesive but would also serve as a protective barrier when applied to surgery or skin sites. In addition, the natural polymers would promote healing due to the inherent properties of the polymers selected.

7 Claims, No Drawings

(56) References Cited

OTHER PUBLICATIONS

Li, et al., Chitosan-alginate hybrid scaffolds for bone tissue engineering, Biomaterials, Jun. 2005, vol. 26, No. 18, pp. 3919-3928.

* cited by examiner

NATURAL POLYMER BASED TISSUE ADHESIVE WITH HEALING PROMOTING PROPERTIES

CROSS-REFERENCE TO RELATED U.S. APPLICATION DATA

This application claims the benefit of U.S. Provisional Patent Application No. 62/605,185 filed on Aug. 4, 2017, the contents of which are hereby incorporated by reference.

FIELD OF THE INVENTION

The invention relates to the field of medical adhesives and sealants. More specifically, the invention relates to a tissue adhesive formed from a mixture of natural polymers in combination with an activating agent that enhances the adhesive properties of the natural polymer mixture.

BACKGROUND OF THE INVENTION

Tissue adhesives for use in the body have very demanding criteria for use and many adhesives used elsewhere, such as cyano-acrylates, cannot be used internally due to toxicity. Also, it is desirable that tissue adhesives for internal use be not only bio-compatible but also absorbable such that there is no need for removal as tissue re-growth proceeds. This creates a challenge for the development of a tissue adhesive for internal use. Skin irritation is also a factor in formulating materials for application to burn or skin donor sites. More benign tissue adhesives have other complications. For example, fibrin-based adhesives have poor mechanical strength and pose a risk of viral infection. Starch-based adhesives require a cross-linking agent which might not be bio-compatible. Thus a tissue adhesive with mechanical strength and good adhesion that is formulated using only bio-compatible and bio-absorbable materials would be advantageous. Totally naturally derived materials are desirable as well.

Several tissue adhesives based on natural polymers have been developed but these formulations typically use a cross-linking agent with aldehyde or amine functional groups along with the natural polymers or modified versions of the natural polymers. For example A. El-Kamel, et al ("*Chitosan and Sodium Alginate-Based Bioadhesive Vaginal Tablets*". AAPS PharmSci 2002: 4 (4) article 44) developed formulations for bio-adhesive tablets as a means for vaginal introduction of metronidazole. In this case, the formulations included 20% of the drug, chitosan and sodium alginate along with microcrystalline cellulose and/or sodium carboxymethylcellulose. Chitosan rods were formed from a paste with acetic acid and dried. These were then cross-linked with glutaraldehyde and compounded with the other ingredients and pressed into tablets. The adhesion of the tablets to rabbit intestinal mucosa was measured and for most formulations observed to be 20 grams/sq. centimeter with one formulation exhibiting 30 grams/sq. centimeter adhesion. The tablets were observed to completely dissolve in distilled water or a pH 4.8 buffer in about 6 hours. Not only is the formulation complicated and uses an aldehyde cross-linking agent but the short life time of the adhesive on exposure to liquids renders it not useful for tissue adhesive applications other than drug release.

Y. Wu, et al ("*A soft tissue adhesive based on aldehyde-sodium alginate and amino-carboxymethyl chitosan preparation through the Schiff reaction*". Frontiers of Material Science, 2017, 11 (3): 215-222. DOI 10:1007/s11706-017-0392-x) explored a soft tissue adhesive formulation. They oxidized the alcohol function of sodium alginate to form aldehyde groups. Carboxymethyl chitosan was modified to produce amino-carboxymethyl chitosan. Mixing various ratios of aqueous solutions of these materials formed a hydrogel in about 10 minutes. The resulting adhesives provided shear adhesion with porcine skin up to 20-30 grams/sq. centimeter. However, this was obtained after pressing the skin sections with a 50 gram loading for 10 minutes. Not only are functionalized natural (rather than totally natural) polymers used in the formulation, the 10 minute press time required to provide the reported adhesion is impractical for a surgical procedure in which the tissue adhesive is used. There was no mention of an adhesive activator or evaluation of durability on exposure to body fluids.

U.S. Patent Application 2017/0326171 describes a hemostatic putty with tissue adhesive properties which includes polysaccharides in the formulation. As opposed to the current invention, this application lists the polysaccharide as only one possible part of a four part composition that includes, in addition to the biopolymer of which chitosan or alginates are possibilities, a secondary polymer (with poly vinyl alcohol cited as the only example), an ionic cross-linker (such as a borate) and a solvent (either water or an organic solvent). There is no combination of natural polymers cited as well as no mention of an activator to enhance adhesion. In addition, although adhesion is mentioned, there is no data presented for adhesion measurements or durability on exposure to bodily fluids.

U.S. Pat. No. 6,341,608 describes use of a tissue adhesive to coat a tumor before removal. Although alginates are listed as possible adhesive materials, there is no citation of a second natural polymer in combination. Also no activator to enhance adhesion is listed and no adhesion data is presented for the tissue adhesive.

Particular applications for a tissue adhesive for which no approved material is currently available are tonsillectomy and adenoidectomy surgeries. These are common procedures that often lead to bleeding and pain. Post-operative pain is exacerbated by swallowing and solid food is generally avoided for the first few days. Improved surgical procedures have been developed that reduce trauma to the delicate mucosal tissue but pain and bleeding continue to be associated with these procedures for many days post-surgery. An adhesive material to form a barrier over the surgery site is desirable but this application is very demanding. The material must provide adhesion to the surgical site (muscle tissue which has been electronically cauterized), be flexible enough to allow flexing of the jaw and yet be mechanically firm enough to show durability in the environment during swallowing. The material used must be easily and simply applied to the surgery site with minimal manipulation and pressure to achieve adhesion. Also, the material must endure the moist environment and exposure to liquids, both saliva and ingested liquids, without loss of integrity for a period of at least two days post-surgery.

The situation is further complicated by the nature of the delicate mucosal tissue. This tissue is by nature wet and this state must be maintained for healing. The wet state prevents the use of classic bandage material due to lack of adhesion to the wet tissue. Furthermore, a classic bandage is a potential choking hazard due to lodging in the throat if it detaches. Obviously, this is an especially serious problem for children, the most common group to experience these surgeries.

Pain and swelling of the traumatized tissue is also an issue and direct topical application of a pain reliever is desirable. However, direct administration of a pain reliever is difficult as well as problematic. Topical administration is also inconsistent other than during an in-patient stay. Typical topical administration of a pain reliever in the throat would be short lived due to washing away or erosion of the pain reliever.

In addition, a means to accelerate healing of the wound site would be beneficial by shortening the recovery time after surgery. Any means to accomplish this must take into consideration maintaining the "wet" state of the mucosal tissue and avoiding any choking hazard from detachment of any device placed in the throat.

A post tonsillectomy device developed for these purposes would also be useful for other procedures in the ear, nose and throat area. A tissue adhesive developed for this purpose also has potential use in other areas such as burn sites or skin donor sites.

Thus there exists a need for a new type of bandage or dressing material as a device that would be suitable for use post tonsillectomy surgery. Ideally, this device would combine a number of functions to alleviate pain, bleeding and trauma. These include an adhesive component such that a typical bandage adhesive that could cause irritation and further trauma to the wound area is not necessary. There should be a component that accelerates healing of the wound site in order to shorten recovery time Optionally, there could be a hemostatic component to control bleeding at the wound site and/or a therapeutic component that alleviates pain and swelling from the surgery trauma. Obviously it would be most beneficial if all components are hypoallergenic as well as bio-compatible. In order to prevent choking hazards if the device loses adhesion and comes free, it would also be beneficial if the device readily broke into small pieces rather than coming free as a single entity.

Despite the obvious need, prior attempts have not been successful in fully addressing or solving the need since only one or two aspects of the stated need are accomplished. The inventors have discovered a means to meet all these needs and develop the novel solution to the problem described herein.

RELATED ART

One example is U.S. patent application 2012/0108509 which describes a means to create an artificial scab for use in airways comprising applying dry powder composed of chitosan plus a partially oxidized polysaccharide such as cellulose or starch. The dry powder is used to adhere to body tissues but no adhesion strength data are reported. There is also no mention of an activating agent to increase adhesion.

U.S. patent application 2016/0151532 describes a hemostatic patch and includes description of use of chitosan but not in combination with an alginate. The claims read to a muco-adhesive and a vasoconstrictant such as neuropeptide Y, epinephrine, etc. and does not report adhesion data or cite an adhesion activator for the powder. No evaluation of durability for internal use is mentioned.

U.S. Pat. No. 8,795,713 describes a mucosal tissue dressing based on methyl cellulose. The aim of this invention is to provide a method to reduce abrasion of a tonsil removal site as seen in claim 1 of the patent. Other than reducing site trauma by avoiding abrasion from solid particles in the throat, the device does not anticipate or provide any of the desirable functions in the problem statement of this invention. The specification section of the '713 patent mentions the use of chitosan, chitin and alginates as part of a long list of potential base polymers for the bandage but not in combination and also does not provide any enabling examples of their use. In addition, no adhesion data is reported and there is no citation of an activator to enhance adhesion. No mention of durability was found.

R. D. Rogers, G. Gurau, J. Shamshina and D. T. Daly in WO 2014172703 describe a combination of fibers of chitin and alginic acid that accelerate wound healing as well as methods to produce and use the fibers. Therapeutics such as Vitamin E can be incorporated into the fibers. The composite fibers were incorporated into a typical external wound bandage and shown to be effective in accelerating wound healing versus either a standard bandage or competitive products currently on the market. The bandage material used incorporated a typical adhesive material for attachment to the skin.

Magdalena Kucharska, Antoni Niekraszewicz, Maria Wiśniewska-Wrona, Kinga Brzoza-Malczewska; ("*Dressing Sponges Made of Chitosan and Chitosan-Alginate Fibrids*". FIBRES & TEXTILES in Eastern Europe July/September 2008, Vol. 16, No. 3 (68)) present a manufacturing process for biological chitosan and chitosan-alginate dressing sponges as well as their biological and physical-mechanical properties. The sponge of chitosan/alginate microfibrids, with an addition of calcium in the in vitro contact with citrate plasma, activates the plasma clotting system to a higher degree, resulting in the shortening of the clotting time of both of the endogenous and exogenous systems when compared with the sponge made of chitosan microfibrids. There is no mention of promotion of activation of the material for improved adhesion or data reporting adhesion.

K. Murakami, H. Aoki, S. Nakamura, S. Nakamura, M. Takikawa, M. Hanzawa, S. Kishimoto, H. Hattori, Y. Tanaka, T. Kiyosawa, Y. Sato and M. Ishihara ("*Hydrogel blends of chitin/chitosan, fucoidan and alginate as healing-impaired wound dressings*"; Biomaterials 31 (2010) 83-90) describe preparation of a hydrogel sheet composed of a blended powder of alginate, chitin/chitosan and fucoidan for evaluation as a wound healing material. The material was more effective at promoting wound healing than no added material or alginate alone. There is no mention of addition of therapeutic agents or of adhesion data. There is also no use of an adhesion activator. Hydrogel sheets were placed on external wound sites and held in place by wrapping with plastic sheets and thus are not amenable as such for the purpose of this invention as well as not meeting all the of desired criteria listed in the problem statement.

S. Honary, M. Maleki and M. Karami ("*The Effect of Chitosan Molecular Weight on the Properties of Alginate/Chitosan Microparticles Containing Prednisolone*", Tropical Journal of Pharmaceutical Research, February 2009, 8 (1); 53-61) describe combinations of solutions of chitosan with alginate and calcium chloride solutions to create microparticles for use as drug delivery and release agents. Although the combination of natural polymers is described, this was not for use as a tissue adhesive and the polymers were in solution when combined, not in powder form. No adhesion activating agent was used in this work. Also, adhesion was measured as the number of particles adhering to a section of rat small intestine, in line with the stated use for drug delivery and not as a tissue adhesive. No mention of durability for internal use was found.

SUMMARY OF THE INVENTION

Thus it can be seen that there exists an unmet need for a tissue adhesive that would be suitable for use post tonsillectomy or other mucosal tissue surgery as well as many other applications. This adhesive could be used in a device that would include adhesive and wound healing accelerating properties as well as a surface layer protective from abrasion at the surgery site. The inventors surprisingly discovered that the powder as formulated provided increased adhesive strength when an activating agent was also used. The activating agent employed is a dilute acid solution preferably a carboxylic acid such as acetic acid, lactic acid or similar. The activating agent could be mixed with the powder to form a gel or it could be sprayed onto the tissue site and the dry powder added to the site, with an optional second spray of the activating agent over the powder. The activating agent could also be sprayed onto the surgery site and the adhesive powder applied as a thin film device using a binding agent that would be dissolved by body fluids. The inventors also unexpectedly found a synergistic effect for increased adhesion with this activation agent by a combination of sodium alginate and chitosan powders in that the combination of the powders provided greater adhesion than either powder when used alone. It was also discovered that durability and toughness of the gel formed could be increased by treating the surface of the gel with a solution of a salt containing a divalent cation such as calcium chloride, calcium acetate or calcium carbonate.

The combination of a mixture of chitosan and sodium alginate powders along with an activation agent in the form of a dilute acid solution provides a high degree of adhesion to the tissue at the surgical site. The combination of chitosan and alginates is well known to promote or accelerate wound healing with many examples in the literature.

In addition, a toughening treatment of the surface of a gel with the above composition with a dilute solution of a calcium salt provides the durability and resistance to bodily fluids to provide abrasion resistance with the underlying gel providing adhesion.

DETAILED DESCRIPTION

A natural polymer is a polymer of plant or animal origin. An alternate term for this is a bio-polymer.

Polysaccharides are polymeric carbohydrate molecules composed of long chains of monosaccharide units bound together by glycosidic linkages, which on complete hydrolysis give the constituent monosaccharides or oligosarrharides. Examples include storage polysaccharides such as starch and glycogen, and structural polysaccharides such as cellulose and chitin.

A partial hydrolysis derivative of a polysaccharide is a derivative in which all or a portion of the side chain functional groups are hydrolysed but there is not complete hydrolysis of the polymeric chain to form monomers. An example is chitosan as a product of hydrolysis of the acetyl amine function of chitin.

A neutralization salt of a polysaccharide is the product of the reaction between a base and the carboxylic acid function of the polysaccharide. An example is the reaction of sodium hydroxide with alginic acid to yield sodium alginate.

An alginate is alginic acid or an ester of alginic acid or a salt of alginic acid.

A dilute solution of an acid is an aqueous solution containing less than 20% by weight of the designated acid. Similarly, a dilute solution of a salt contains less than 20% by weight of the salt.

A toughening treatment of an adhesive gel is a chemical cross-linking that allows the gel to retain firmness and/or integrity or reduce fluid absorption when exposed to bodily fluids.

A workable gel is one which is easily manipulated for placement at the desired site.

The device of this invention is a combination of materials which meet the criteria as outlined above. The materials suitable for this device include combinations of compounds such as chitosan or chitin powder, alginic acid or salts of this acid. Optionally, therapeutic compounds can be added to the powder (e.g. vitamins, analgesic. (such as acetaminophen or an NSAID), vasoconstrictive (such as neuropeptide Y, epinephrine) or anesthetic (examples include, but are not limited to: lidocaine, benzocaine, bupivacaine, levobupivacaine, ropivacaine, etidocaine or articaine) in any combination. Also an anti-infective (such as Primaxin or Pentamycetin) could also be incorporated into the device as a means of immediate action to prevent infection with the chitin/chitosan providing longer term infection control.

The material as described could be placed inside a cavity which is then closed with the adhesive or sutures, used to create an external dressing for a surgery site by application as a gel, thin film device or dry powder, or any methods in combination.

For example, as part of the tonsillectomy surgery a pouch or flap could be formed at the surgery site and a device incorporating the combined materials could be placed inside the pouch or flap before the site is closed. The device could be in the form of a gel, lozenge or similar form that is of suitable size or enclosed in an thin film, envelope or capsule formed of a material that is quickly dissolved by the body for rapid release of the active ingredients.

Another option, either in combination with the implanted device described above or separately, is to apply the adhesive mixture as a dry powder externally to the surgery site after the site is closed. This would provide control of bleeding, increased rate of wound healing as well as alleviation of pain and swelling. In this case, no, additional materials for adhesion, other than the adhesion activator described, would be required due to the adhesive properties of the sodium alginate:chitosan powder. The nature of the powder applied in this manner rather than as a classic bandage would avoid creating a choking hazard as the material would be released in small, friable pieces that could be either swallowed with no harm or ejected orally. The lack of a separate adhesive compound would reduce the possibility of irritation of mucosal tissue.

Another option is to incorporate the adhesive powder into a thin film device with a binding agent that would be dissolved by body fluids. The film could then be placed onto the surgery site (optionally after the site is wet with an activating compound) to provide a thin layer of the powder with the desired properties as described above. Optionally, once in place the thin film could be sprayed with the activating compound and/or subjected to a toughening treatment with a compound having divalent cation to increase resistance of the film to bodily fluids while maintaining adhesion.

Yet another option is to incorporate the adhesive powder into a gel by mixing with an aqueous solution of the activating compound. This gel would then be placed onto the surgery site for adhesion to form a protective device. Optionally, once in place the gel could be subjected to a toughening treatment with a compound having a divalent cation to increase resistance of the gel to bodily fluids while maintaining adhesion.

Alternatively, the gel as described above could be applied externally to a skin donor or graft site (for example) for protection and to promote healing. In this case, the optional toughening treatment might not be necessary.

Thus it is seen that the desired properties and functions of a protective device that also promotes healing for post-surgery use may be achieved through a novel combination of compounds and thus provide a viable solution to a problem for which no practical solution has previously existed.

With no additional adhesives needed and the healing properties of the combined powders, the formulations detailed here could to find uses in other applications such as burn sites and skin donor sites.

EXAMPLES

In all examples the chitosan used was high molecular weight chitosan obtained from Sigma-Aldrich and the sodium alginate was obtained from willpowder.com. White vinegar was used as the acetic acid source. The vinegar and other materials were obtained locally.

Shear Testing for Adhesive Strength:

The shear tests (see K. Vakalopoulos, et al; "*Mechanical Strength and Rheological Properties of Tissue Adhesives With Regard to Colorectal Anastomosis*"; *Annals of Surgery*, Volume 261, Number 2, February 2015, pp 323-331) were performed on specimens of thin sliced (⅛") beef round bottom that were 3 centimeters by 4 centimeters in size to provide 12 square centimeters for the adhesion surface. These specimens were washed with water and blotted dry with a paper towel. Each surface was then irrigated with the activating agent solution (~1 ml. per surface) and then 0.30 grams of the powder to be tested was sprinkled uniformly on each surface. The two adhesion test surfaces were again irrigated with the activating agent and the two surfaces joined. The specimen was pressed with 2 pounds of weight for 5 seconds before being placed in the shear test rig such that one surface was held stationary and the other was supporting the added weight. Weight was then added incrementally until separation of the specimen occurred. Results are shown in Table I.

TABLE I

| Sample ID | Adhesive Used | Activating Agent | Separation Weight Grams |
|---|---|---|---|
| Comparative A | 75:25 Sodium Alginate:Chitosan | Normal Saline | 96.6 |
| Comparative B | Sodium Alginate | 4% Acetic Acid | 163.0 |
| Comparative C | Chitosan | 4% Acetic Acid | 128.0 |
| Example 1 | 75:25 Sodium Alginate:Chitosan | 4% Acetic Acid | 274.5 |
| Example 2 | 50:50 Sodium Alginate:Chitosan | 4% Acetic Acid | 225.0 |
| Example 3 | 25:75 Sodium Alginate:Chitosan | 4% Acetic Acid | 116.7 |
| Example 4 | 75:25 Sodium Alginate:Chitosan | 4% Lactic Acid | 193.7 |

Comparative Example A versus Example 1 show that the dilute acetic acid activator provides significantly enhanced adhesion versus normal saline. Comparative Examples B and C versus Examples 1, 2 and 4 show enhanced adhesion for the mixture of the two natural polymers over the adhesion observed for the individual polymers. Example 1 demonstrates an adhesion of 22.9 grams/square centimeter.

The procedure as described above was followed with the addition of 0.10 gram of a therapeutic agent to the 75:25 sodium alginate:chitosan powder. In Example 5, acetaminophen was used as the therapeutic agent and in Example 6 the therapeutic agent was naproxen. As can be seen in Table II, there was a small decrease in adhesive strength versus Example 1 with the therapeutic added but the adhesive strength was still greater than all Examples other than Example 1. Results are summarized in Table II.

TABLE II

| Sample ID | Therapeutic Used | Adhesion Decrease | Separation Weight Grams |
|---|---|---|---|
| Example 5 | Acetaminophen | 7% | 255.5 |
| Example 6 | Naproxen | 12% | 241.5 |

Table II illustrates that therapeutic agents may be added to the adhesive formulation with only a small decrease in adhesive strength to maintain adhesion within a range appropriate for the applications cited.

Gel Durability Testing:

A gel was formed by adding first 6 ml. of the activating agent to a small ceramic cup, followed by 0.35 grams of 75:25 Sodium Alginate:Chitosan. This was thoroughly mixed to form a soft and workable gel. This was used as the Comparative Example D and to this was added 10 ml. of normal saline solution. This was then covered to prevent evaporation and allowed to sit for 48 hours. In Examples 7 and 8 the same procedure was used with the exception that the gel was treated with a 2% by weight aqueous solution of a calcium salt before being exposed to saline. Calcium chloride was used in Example 7 and calcium carbonate in Example 8. After the saline was removed the gel was weighed and subjected to a pressurized water jet to determine integrity. Water pressure at gel breakup with a normal water stream from a faucet or a waterpik type device was observed. Results are shown in Table III.

TABLE III

| Sample ID | Calcium Salt Used | Activating Agent | Weight Gain | Gel Integrity |
|---|---|---|---|---|
| Comparative D | None | 4% Acetic Acid | 5.2 grams | Soft Gel - No integrity |
| Example 7 | Calcium chloride | 4% Acetic Acid | 4.0 grams | Firm Gel Breakup with water pik at 80 psig |
| Example 8 | Calcium carbonate | 4% Acetic Acid | 6.0 grams | Medium Firm Gel Integrity lost with normal faucet stream |

Comparative Example D versus Examples 7 and 8 show that the resistance of the gel to body fluid is improved with the calcium treatment for retention of the integrity of the gel. Fluid absorption is decreased with the calcium chloride treatment.

What is claimed is:

1. A tissue adhesive for application to a tissue site, said tissue adhesive comprising:
    a gel having adhesive properties comprising a mixture of natural polymers, said natural polymer mixture comprising an alginate and chitosan, wherein the ratio of alginate to chitosan is between 25:75 and 75:25, and wherein said gel comprises a first surface for application to said tissue site and a second surface opposite to said first surface; and an activating agent which enhances said adhesive properties of said gel, wherein said activating agent comprises a 4% acetic acid solution;

wherein said gel is provided with a surface treatment to toughen a surface of said gel by treating said second surface of said gel with a dilute aqueous solution of a calcium salt.

2. The tissue adhesive of claim 1 wherein said alginate comprises sodium alginate.

3. The tissue adhesive of claim 2 wherein the ratio of sodium alginate to chitosan is 25:75.

4. The tissue adhesive of claim 2 wherein the ratio of sodium alginate to chitosan is 75:25.

5. The tissue adhesive of claim 1 wherein said tissue adhesive further comprises at least one from the group consisting of an analgesic, an anesthetic and a vasoconstrictive compound.

6. The tissue adhesive of claim 1 wherein said calcium salt comprises at least one from the group consisting of calcium chloride, calcium acetate and calcium carbonate.

7. The tissue adhesive of claim 1 wherein said tissue site comprises at least one from the group consisting of a surgical site created during tonsillectomy surgery, a surgical site created during adenoidal surgery, a burn site, a skin donor site, a skin graft site and a joinder site between two pieces of tissue.

* * * * *